United States Patent [19]
Hall

[11] Patent Number: 5,715,840
[45] Date of Patent: Feb. 10, 1998

[54] SNORE-REPRESSING MOUTHPIECE

[76] Inventor: Thomas D. Hall, 7204 Yama Way, Bakersfield, Calif. 93308-6409

[21] Appl. No.: 669,959

[22] Filed: Jun. 25, 1996

[51] Int. Cl.$^6$ .................................................. A61F 5/56
[52] U.S. Cl. ........................ 128/848; 128/859; 128/861; 602/902
[58] Field of Search .............................. 128/846, 848, 128/859–862; 2/2; 433/6, 7

[56] References Cited

U.S. PATENT DOCUMENTS

| | | | |
|---|---|---|---|
| 2,521,039 | 9/1950 | Carpenter | 128/861 |
| 5,313,960 | 5/1994 | Tomasi | 128/848 |
| 5,365,945 | 11/1994 | Halstrom | 128/848 |
| 5,427,117 | 6/1995 | Thornton | 128/848 |

*Primary Examiner*—Michael A. Brown
*Attorney, Agent, or Firm*—Robert M. Sperry

[57] ABSTRACT

An improved snore-preventing device having a mouthpiece insertable into a user's mouth and having an upwardly-facing trough member and a downwardly-facing trough member secured together by a plurality of spacer members in a manner to ensure proper positioning of the user's jaws and having a quantity of thermo-setting resin contained in each of said troughs to fit said mouthpiece to an individual user.

5 Claims, 1 Drawing Sheet

SNORE-REPRESSING MOUTHPIECE

FIELD OF INVENTION

This invention relates to snore repression devices and is particularly directed to mouthpieces for preventing a sleeping person from snoring.

PRIOR ART

One of the most frequent causes of marital disputes is snoring. Snoring often interferes with one's bed partner falling asleep, yet the person doing the snoring is usually asleep and, hence, is unaware that they are snoring. Consequently, it is common for the snorer to deny that they are doing it, while their bed partner insists that they are. Thus, arguments result. Numerous devices have been proposed heretofore for preventing or overcoming snoring. Unfortunately, many of the prior art snore-preventers are based upon so-called "home remedies", which have little or no basis in fact and, therefore, are of little or no value in reducing or preventing snoring. Many of the prior art snore-preventing devises are complex and expensive to produce or are complicated and uncomfortable to use. Some prior art snore-preventing devices are actually dangerous and virtually none of the prior art snore preventing devices has been effective.

BRIEF SUMMARY AND OBJECTS OF INVENTION

These disadvantages of the prior art are overcome with the present invention and an improved snore-preventing device is provided which is inexpensive to produce, simple and comfortable to use and which is highly effective in preventing snoring The advantages of the present invention are preferably attained by providing an improved snore-preventing device comprising a mouthpiece insertable into a user's mouth and having an upwardly-facing trough member and a downwardly-facing trough member secured together by a plurality of spacer members in a manner to ensure proper positioning of the user's jaws and having a quantity of thermo-setting resin contained in each of said troughs to fit said mouthpiece to an individual user.

Accordingly, it is an object of the present invention to provide an improved snore-preventing device.

Another object of the present invention is to provide an improved snore-preventing device which is inexpensive to produce.

An additional object of the present invention is to provide an improved snore-preventing device which is simple and comfortable to use.

A further object of the present invention is to provide an improved snore-preventing device which is highly effective in preventing snoring.

A specific object of the present invention is to provide an improved snore-preventing device comprising a mouthpiece insertable into a user's mouth and having an upwardly-facing trough member and a downwardly-facing trough member secured together by a plurality of spacer members in a manner to ensure proper positioning of the user's jaws and having a quantity of thermo-setting resin contained in each of said troughs to fit said mouthpiece to an individual user.

These and other objects and features of the present invention will be apparent from the following detailed description, taken with reference to the figures of the accompanying drawing.

DETAILED DESCRIPTION OF THE INVENTION

Figure 1:
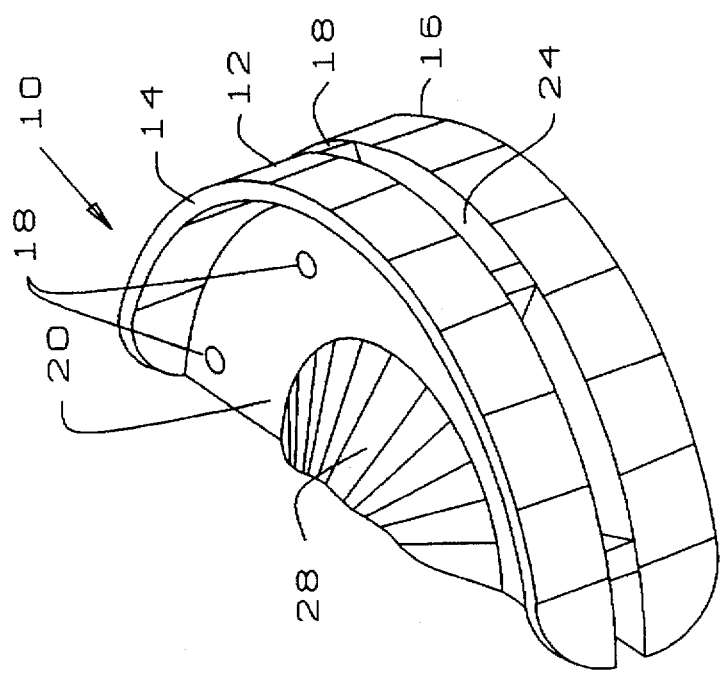
FIG. 1 is an isometric view of a snore-preventing device embodying the present invention.
Figure 2:
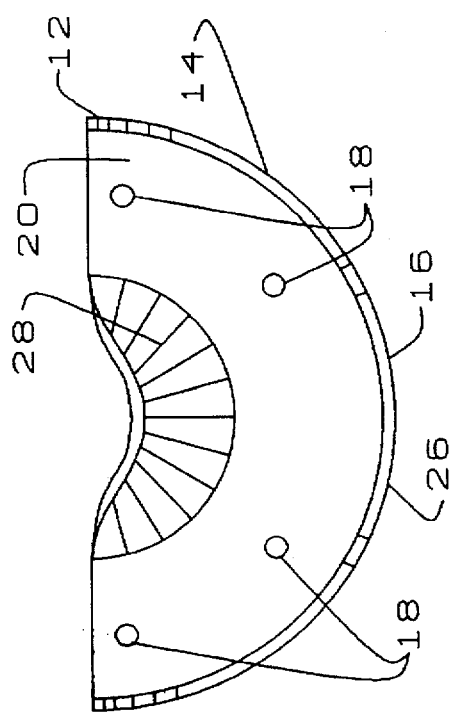
FIG. 2 is a plan view of the snore-producing device of FIG. 1.

In that form of the present invention chosen for purposes of illustration in the drawing, FIG. 1 shows a snore-preventing device, indicated generally at 10, comprising a mouthpiece 12 having a first generally U-shaped trough member 14 and a second generally U-shaped trough member 16 joined by a plurality of hollow support members 18. As shown, the first trough member 14 has an open upper surface 20, while the second trough member 16 has an open lower surface 22 and the spacer members 18 serve to position the first trough member 14 and second trough member 16 16 separated by a space 24, as seen at 26 in FIGS. 2 and 3. The inner walls 28 and 30 of the first and second trough members 14 and 16, respectively, incline rearwardly, forming lunate surfaces 19 which creates a suction that draws the patient's tongue to a forward position which opens the patient's airway and reduces snoring. Finally, for fitting, a quantity of suitable thermosetting resin in placed in each of the trough members 14 and 16, as seen at 32 in FIG. 3, and flows through the hollow support members 18 to secure the trough members 14 and 16 together. This serves to maintain the trough members 14 and 16 is fixed relation, which assures that the jaws will be held in the desired position while the patient is sleeping. Obviously, the resin 32 must be of a type which will not adhere to the enamel of a patient's teeth.

Figure 3:
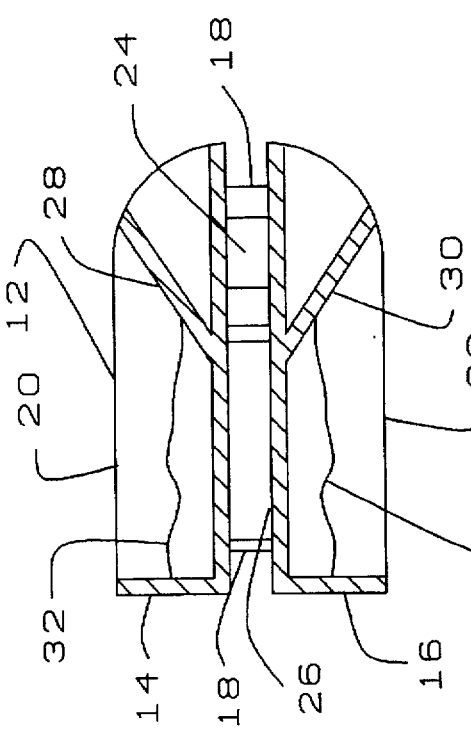
FIG. 3 is a vertical section through the snore-preventing device of FIG. 1 showing the thermo-setting resin in place for fitting the device of the present invention to a particular user.

To fit the mouthpiece 12 to a user, the thermo-setting resin 32 is placed in each of the trough members 14 and 16, as seen in FIG. 3, and the mouthpiece 12 is placed in the user's mouth. The user, then closes his mouth to grip the mouthpiece 12 and to cause his teeth to form impressions in the thermo-setting resin 32 and to force the resin 32 to flow through the hollow support members 18. The resin is then allowed to set, thereby securing the trough members 14 and 16 in the desired position. When the resin 32 has set, the mouthpiece 12 is removed from the user's mouth and may be reinserted to test for proper and comfortable fit. Thereafter, when the user is about to go to sleep, they place the mouthpiece 12 in their mouth and close their mouth to lightly grip the mouthpiece. When this is done, the mouth piece 12 serves to maintain the user's jaws in proper relation to prevent snoring and the space 28, between the first trough member 14 and second trough member 16, provides ample air space for breathing. Also, the lunate surfaces 28 and 30 serve to create a suction which draws the patient's tongue forward, ensuring that the patient's airway is open. The resin 32 ensures that the mouthpiece will have a tight, yet comfortable, fit, allowing the user to wear the mouthpiece 12 throughout the night to prevent snoring without interfering with the user's sleep.

Obviously, numerous variations and modifications can be made without departing from the spirit of the present invention. Therefore, it should be clearly understood that the form of the present invention described above and shown in the figures of the accompanying drawing are illustrative only and are not intended to limit the scope of the present invention.

What is claimed is:

1. A snore-repressing device comprising:

a mouthpiece having a pair of generally U-shaped trough members of uniform and constant dimensions with one of said trough members opening upward and the other of said trough members opening downward, and at least one hollow rigid spacer member mounted between said trough members and serving to maintain said trough members in fixed spaced relation with the lower of said trough members being maintained downward and foreward of the upper trough member.

2. The device of claim 1 further comprising:

a quantity of thermo-setting resin located in each of said trough members.

3. The device of claim 2 wherein:

said resin is placed in said trough members prior to setting and is allowed to set in situ.

4. The device of claim 3 wherein:

said device is placed in a user's mouth and is gripped by the user's teeth while said resin is setting to fit said mouthpiece to the user.

5. The device of claim 1 wherein:

the inner walls of said trough members are inclined rearwardly.

* * * * *